United States Patent [19]

Ferrer

[11] Patent Number: 4,582,054

[45] Date of Patent: Apr. 15, 1986

[54] PORTABLE BREATHING APPARATUS

[76] Inventor: Lilly Ferrer, 31 Beachwalk, Island Park, N.Y. 11558

[21] Appl. No.: 616,486

[22] Filed: Jun. 1, 1984

[51] Int. Cl.$^4$ ............................................. A61M 15/00
[52] U.S. Cl. .......................... 128/200.23; 128/204.13; 128/205.25
[58] Field of Search ............ 128/205.25, 200.23, 128/206.12, 206.21, 206.24, 202.13, 204.13; 222/131

[56] References Cited

U.S. PATENT DOCUMENTS

| | | | |
|---|---|---|---|
| 2,700,578 | 1/1955 | Efford | 222/131 |
| 2,965,100 | 12/1960 | Bridges | 128/200.23 |
| 3,019,788 | 2/1962 | Hughes | 128/205.25 |
| 4,119,097 | 10/1978 | Spector | 128/205.25 |
| 4,440,163 | 4/1984 | Spergel | 128/205.25 |

FOREIGN PATENT DOCUMENTS

| | | | |
|---|---|---|---|
| 113069 | 8/1961 | Denmark | 128/200.23 |
| 1323477 | 2/1963 | France | 128/202.13 |
| 150232 | 9/1920 | United Kingdom | 128/206.24 |

Primary Examiner—Henry J. Recla
Attorney, Agent, or Firm—Scully, Scott, Murphy & Presser

[57] ABSTRACT

A portable breathing apparatus for the provision of an emergency supply of an oxygen-rich gas, such as air, and more particularly, a portable breathing apparatus which is specifically adapted to assist in preventing the loss of life or the sustaining of injuries which are caused by smoke inhalation during fires.

10 Claims, 8 Drawing Figures

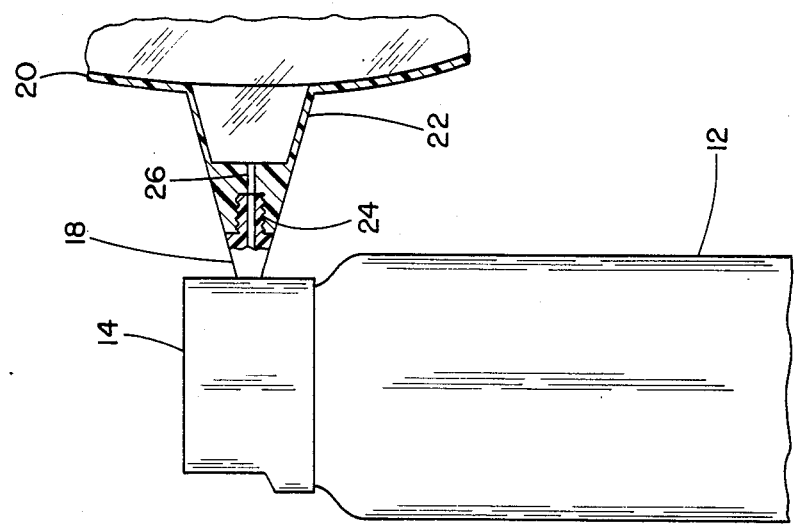
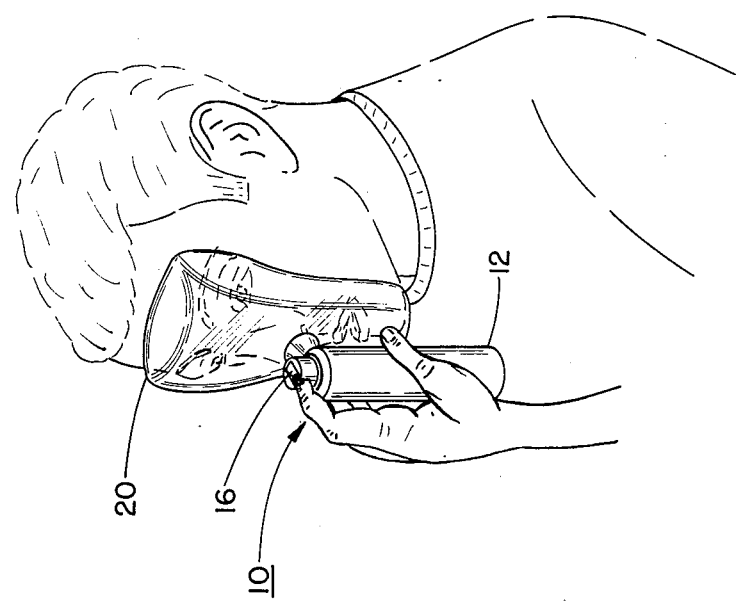
FIG.1
FIG.2

PORTABLE BREATHING APPARATUS

BACKGROUND OF THE INVENTION

1. Field of the Invention

The present invention relates to a portable breathing apparatus for the provision of an emergency supply of an oxygen-rich gas, such as air, and more particularly, relates to a portable breathing apparatus which is specifically adapted to assist in preventing the loss of life or the sustaining of injuries which are caused by smoke inhalation during fires.

Among the many hazards to which human beings are normally exposed in everyday life, fires present the most serious dangers to health and life, especially fires which are encountered in hotels, office and apartment buildings, particularly modern high rise structures, and even in single-family dwellings. Although most high-rise structures and large dwellings are constructed of materials such as to be essentially fireproof in order to comply with various local and state fire codes and ordinances, these structures, and their frequently flammmable contents and furnishings are not necessarily smoke-proof. It is common knowledge that most injuries and deaths which are sustained as the result of fires in which the victims have been trapped in either hotel rooms, offices, or dwellings are not caused by the actual flames, but are rather the consequence of inhalation of smoke and other noxious fumes from the fire, which readily leads to serious internal injuries, such as irreversible lung and brain damage, and even death through asphyxiation.

2. Discussion of the Prior Art

Various attempts have been made to reduce the extent of injuries and loss of human life which is caused by fires encountered in such dwellings. Thus, many dwellings, hotels, and offices, especially of the high-rise type, provide for fire alarms in order to timely alert the occupants, and to assist them in escaping the fires through well-defined and identified stairwells and exits. Other such structures, besides the presence of fire alarms, incorporate extensive sprinkler systems which upon the sensing of fire and/or smoke will automatically activate and attempt to either retard the spreading of the fire or even extinguish the fire completely.

All of these foregoing measures, and numerous other types of devices have been developed to alert the occupants of the dwellings, hotels and offices to the presence of fire and smoke, and to enable them to leave the premises quickly Nevertheless, notwithstanding these warning and preventive measures, quite frequently the fires are detected only belatedly and in many instances, especially when the structures are not equipped with fire preventive and alerting arrangements, the fire may cause the occupants to be entrapped in a fire and smoke-filled environments and exposed to serious injury and possibly death. This is particularly the case at night in dwellings in which children or infants sleep in separate bedrooms, and upon the occurrence of a fire which often spreads extremely rapidly with intense propagation of smoke and noxious fumes, causes them to be trapped and frequently asphyxiated with the parents or adults being prevented from reaching the children due to the presence of the flames, or being unable to locate the children because of the heavy smoke which is being generated; which can also cause asphyxiation of the searching adults.

Accordingly, of the present invention contemplates the provision of a portable breathing apparatus which will provide an emergency supply of an oxygen-rich gas, such as breathing air, for a limited period of time so as to afford a user who is caught in a burning environment a great degree of protection from smoke inhalation which can cause possible asphyxiation, and allowing the user additional time to establish a safe escape route from the location of the fire. Moreover, the user of the inventive portable breathing apparatus will also be enabled to move about the smoke-filled locale so as to locate other trapped occupants and to lead them to safety, thereby appreciably reducing injuries and loss of life due to fires, and especially as a result of smoke inhalation and asphyxiation.

Among devices and aids which have been developed in the technology for assisting the occupants of dwellings, hotels and offices, particularly high-rise structures, to escape from the ravages of fire and smoke, and to possibly rescue other trapped occupants, while ameliorating or avoiding any injuries or deaths due to smoke inhalation and possible asphyxiation, are various types of apparatuses which will provide for an emergency oxygen or air supply. Generally, these apparatuses are relatively cumbersome and complex and are primarily for use by firefighters entering such occupied building structures and enabling their searching for any occupants who may be trapped in the burning structure.

Among the apparatuses which may be used to advantage by firefighters or other rescue personnel entering burning dwellings or hotel and office buildings, Watanabe U.S. Pat. No. 1,331,601 discloses a respirator incorporating a face mask strapped to the face of a user, which may be connected to large canisters containing air and which are supported on the back of the user. This is a relatively cumbersome and expensive device and is primarily designed for use by skilled firefighters and rescue personnel. Similarly, Marina U.S. Pat. No. 2,897,817 discloses an oxygen mask with a head strap, which may be combined with a container supported directly on the mask and which includes valving means for dispensing an oxygen-rich gas into the mask. This is primarily a diving mask used for subsea exploration.

Morrison U.S. Pat. No. 3,186,407 discloses a canister containing an oxygen-rich gas which is connected to a face mask covering the nose and mouth of a user, and which is adapted to provide a limited supply of the gas into the mask. However, the structure thereof is relatively heavy and cumbersome and is primarily adapted for use by skilled firefighters.

Spector U.S. Pat. No. 4,119,097 discloses a somewhat more compact emergency oxygen supply device including a small canister of the aerosol-can type which is attached to a bellows and a face mask covering the nostrils and the mouth of a user, wherein oxygen is cycled through the bellows to provide oxygen to a person suffering from emphysema or similar respiratory ailments. Again, this is a relatively complex and expensive device which may be adapted for professional use by firefighters or personnel having some degree of skill in the use and application of such breathing devices.

Numerous other types of breathing devices are disclosed in Nakanishi U.S. Pat. No. 3,820,538; Davis et al. U.S. Pat. No. 4,126,131; Kahan U.S. Pat. No. 2,856,922; Updegraff U.S. Pat. No. 3,045,671; Gattone U.S. Pat. No. 3,136,312; Petrahai U.S. Pat. No. 3,604,416; Hanson U.S. Pat. No. 4,078,561; Bickford U.S. Pat. No. 3,565,068; and Henneman et al. U.S. Pat. No. 3,976,063.

Although all of the foregoing disclosures, and numerous other prior art devices, provide for the emergency supply of oxygen or a breathing gas to a user, and may be readily employed by persons trapped in building fires, these devices are generally of relatively complex and cumbersome designs so that a person trapped in a fire or a smoke-filled environment who may be relatively unsophisticated or unskilled in the use of such equipment, or may be of tender years, is frequently unable to operate such devices.

SUMMARY OF THE INVENTION

Accordingly, in order to overcome the limitations encountered in the prior art, the present invention provides a portable breathing apparatus for the provision of an emergency supply of an oxygen-rich gas, such as air or the like, which is extremely simple and inexpensive in construction, and which may be readily manipulated and used without the need for any special skills to advantage by an occupant of a dwelling, office or hotel trapped therein by fire in a smoke-filled environment which can readily lead to serious injury or asphyxiation.

The inventive portable breathing apparatus includes an aerosol-type canister or container filled with an oxygen-rich gas, such as air, under a relatively low pressure which may be readily carried by one hand, and which has a dispensing valve operable through depressing a suitable pushbutton arranged on the exterior of the container, as is well known in the construction of aerosol-type cans, and the outlet or dispensing orifice having a face mask of a substantially transparent and basically flexible plastic material attached thereto, which mask will fit over and adapt itself to the facial physiognomy of a user so as to cover the mouth, nasal passages and the eyes and to thereby prevent the entry of any smoke or noxious gases generated by the fire from entering the interior of the face mask when pressed against the face. The breathing gas contained in the container may be readily expelled into the face mask by simply depressing the actuating pushbutton of the container so as to provide a supply of breathing air to the user, while the slightly higher pressure of the breathing air discharged in the face mask from the container will prevent entry thereinto of the noxious smoke of the surrounding environment.

Pursuant to one particular embodiment of the invention, the container or canister may include water which is admixed with the oxygen-rich gas to provide a discharge spray for moistening of the lips and nasal passages of a user. With such structure, at least the lower half of the face mask is filled with a gas-permeable sponge-like material which will preclude the water from the air-water spray entering the mask from the container from being sprayed into the eyes and obscuring the vision of the user of the mask.

The extremely lightweight construction and simplicity in operation of the device eliminates the need for head straps and other attaching devices inasmuch as the entire apparatus can be held and manipulated with one hand, so as to allow the other hand of the user to remain free for use in opening doors or windows, and possibly leading or pulling other trapped occupants of the structure from the location of the fire.

Accordingly, it is a primary object of the present invention to provide a portable breathing apparatus providing a user with an emergency supply of an oxygen-rich gas, such as breathable air.

A more specific object of the present invention is to provide a portable breathing apparatus wherein an emergency supply of an oxygen-rich gas is contained in a container of the aerosol-can type under a relatively low superatmospheric pressure, and wherein a transparent and flexible plastic face mask is attached to a dispensing orifice of the container and is adapted to receive a selectively intermittent or continuous supply of gas from the container through the simple manipulation of a pushbutton or lever-actuated valve which is arranged on the container.

Yet another object of the present invention is to provide a portable breathing apparatus of the type described hereinabove, wherein the apparatus can be held and manipulated by the user while employing only a single hand, and in which the device can be operated by simply depressing a pushbutton with one finger of that hand or depressing a lever extending along the container so as to release an amount of the gas from the container into a face mask which is pressed against a face of a user.

DETAILED DESCRIPTION

Further features and advantages of the invention may now be ascertained from the following detailed description of preferred embodiments of the portable breathing apparatus providing for an emergency supply of an oxygen-rich gas or the like; taken in conjunction with the accompanying drawings; in which:

FIG. 1 illustrates a perspective view of one embodiment of a portable breathing apparatus of the invention while in condition of use;

FIG. 2 illustrates a fragmentary side elevational view of the breathing apparatus of FIG. 1, shown partly in section;

DETAILED DESCRIPTION

Figure 3:
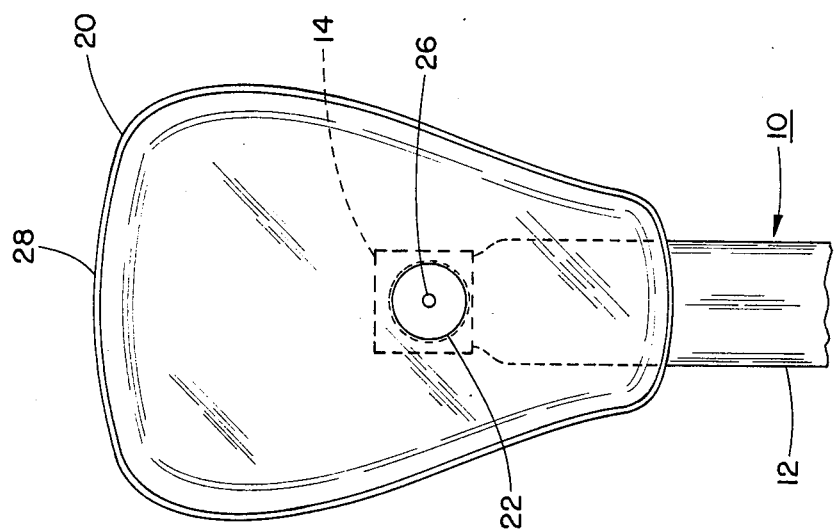
FIG. 3 illustrates a front elevational view of the breathing apparatus of FIG. 2.

Referring now in detail to the embodiment of the portable breathing apparatus as illustrated in FIGS. 1 to 3 of the drawings, the inventive breathing apparatus 10 includes a generally cylindrical sealed container 12 which may be of the aerosol can-type as is well known in the art and which is widely employed for the dispensing of sprays of deodorants, shaving cream, disinfectants or the like. In this instance, the container is filled with an oxygen-rich gas, such as air or an air-oxygen mixture under relatively low superatmospheric pressure, possibly a few atmospheres. The upper end 14 of the container is provided with a depressable pushbutton-type valving device 16, as is well known in the aerosol can art, and which may be depressed by the index finger of a user while holding the container 12 with the same hand. Connected to an extension 18 having a dispensing orifice communicating with the valving device 16, is a face mask 20 which is preferably constructed from a transparent molded plastic material having a certain degree of flexibility or resilience so as to be generally conformable with the facial contour of a user when pressed thereagainst. Preferably, the mask 20 should be dimensioned and shaped so as to substantially cover the space about the mouth, nostrils and eyes of a user when pressed against the latter's face while providing breathing space therebetween.

A projecting member 22 of generally tubular configuration, which may be of molded plastic material, is fastened to the outer surface of the face mask 20 and may include a threaded portion 24 adapted to be screwed onto a threaded portion on the extension 18 on the head portion 14 of the container 12. A central passageway 26 provided for in the tubular extension 22 communicates with the discharge of the valving device 16, whereby depression of the valving device 16 will cause a quantity of the oxygen-rich gas to flow from the container 12 through the passageway 26 into the interior space of the face mask 20. Although the connection between the face mask 20 and the container 12 is illustrated as being a threaded arrangement 24 so that upon exhaustion of the contents of the container 12, the latter may be unscrewed from the face mask 20 and replaced by a filled replacement container 12, it is also possible to contemplate a construction in which the face mask 20 is being permanently fastened to or integrally formed with the container 12.

When desired, the container 12 may be encased in a heat-insulating material such that any undue increase in the external temperature will not adversely affect the gaseous contents thereof. Moreover, in order to ensure that the contents of the container have not been tampered with during storage in a hotel room, office or dwelling, the entire apparatus 10 may be enclosed in a sealed, thin-walled transparent plastic bag (not shown) which can be easily ripped open in case of emergency.

In order to provide an improved degree of sealing between the face mask 20 and the face of a user, at times it may be desirable to provide a seal or gasket-like member 28 extending about the rim of the face mask 20 which is adapted to contact the face. Such a seal may be constituted of a sponge-like or resilient material, such as felt, foamed plastic or the like.

Figure 4:
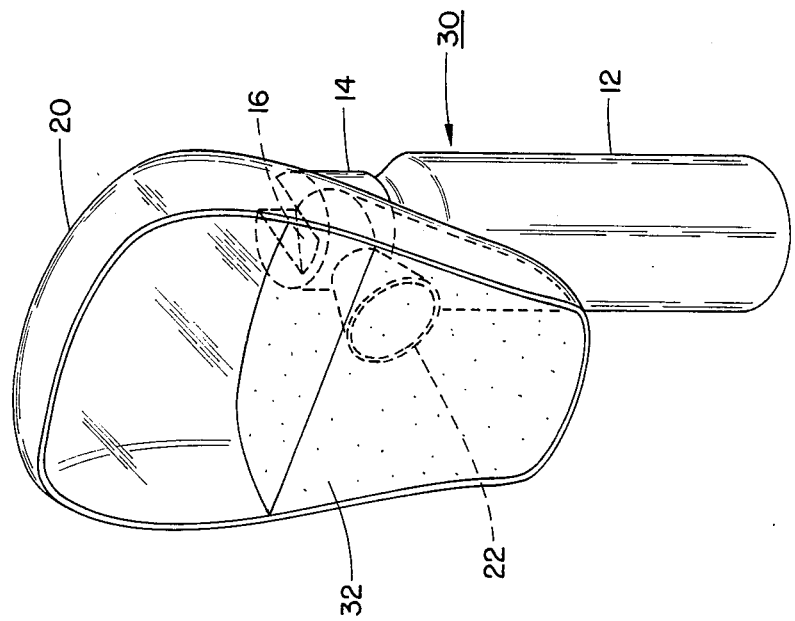
FIG. 4 illustrates a perspective view of a modified embodiment of the inventive breathing apparatus.

Referring to the embodiment of the breathing apparatus 30 as illustrated in FIG. 4 of the drawings, wherein components which are similar to or identical with those in the embodiment of FIGS. 1 to 3 are identified by the same reference numerals; the lower portion of the face mask 20 has the interior thereof filled with a sponge-like, porous material 32 adapted to cover the nostrils and the mouth portion of the face of a user but leaving the eyes capable of seeing through the mask. In this embodiment, the gas which is adapted to be ejected from the container 12 into the face mask 20 is admixed with water contained in the former so as to form a gas-water spray, inasmuch as during the use of oxygen-rich gases and exposure to smoke, the lips of a user may tend to dry and blister. However, the gas-permeable or porous sponge material 32, while permitting the passage of the breathable gas therethrough towards the mouth and nostrils of the user, will inhibit water from being sprayed in the eyes of the user which are positioned in the upper portion of the mask 20.

Reverting the the embodiments illustrated in FIGS. 5 through 8 of the drawings, in which similar or identical components are identified with the same reference numerals a those in FIGS. 1 to 3, there are disclosed different embodiments of the container and valve-actuating mechanism for dispensing a quantity or flow of the oxygen-rich gas or air into the face masks from the container.

Figure 5:
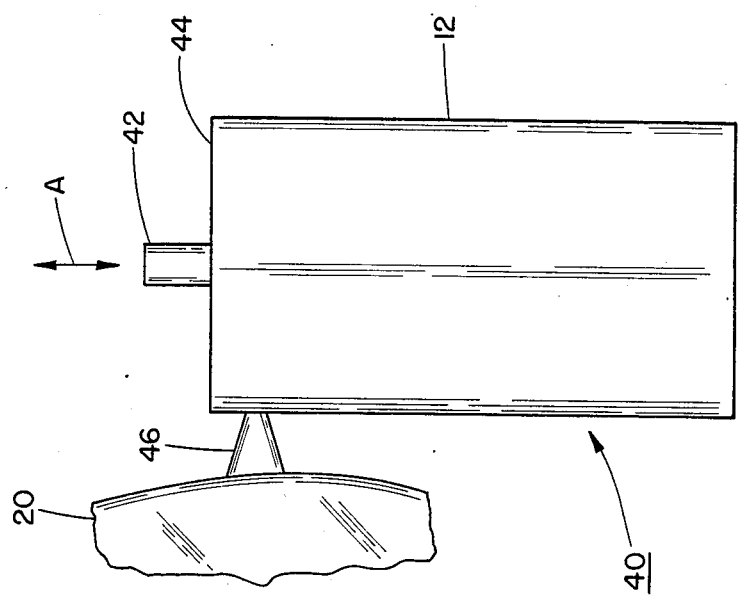

In the embodiment of FIG. 5 the breathing apparatus 40 has the face mask 20 attached to one side of the container 12 proximate the upper end thereof, and incorporates a vertically depressable pushbutton 42 centrally located on the upper end surface 44 of the container, the pushbutton being actuatable in the direction of arrow A, whereby upon depression of the pushbutton 42 a quantity of the breathing air is discharged through the connector 46 from the interior of the container 12 into the face mask 20.

Figure 6:
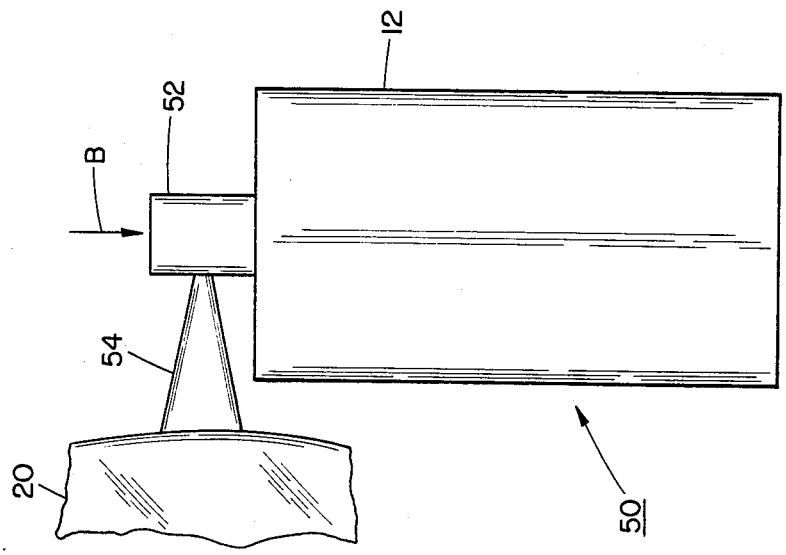
FIGS. 5 through 8, respectively, illustrate fragmentary side elevational views of different embodiments of the inventive breathing apparatus.

In the embodiment of FIG. 6 of the drawings, the breathing apparatus 50 has the face mask 30 connected directly to the vertically actuatable pushbutton 52 which may be depressed in the direction of arrow B so as to discharge a flow of the gas from the container 12 through the connector 54 into the face mask 20.

Figure 7:
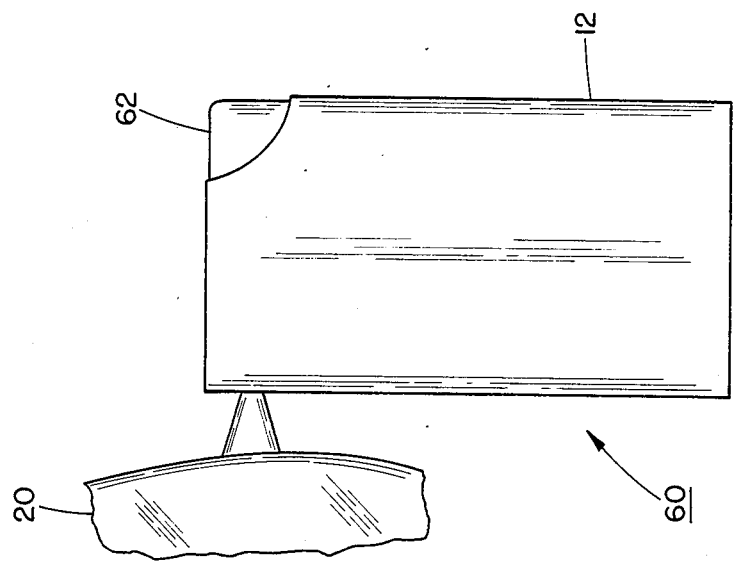

In the embodiment of FIG. 7, the breathing apparatus 60 has the face mask 20 fastened to the container 12 in a manner similar to that of FIG. 5 of the drawings; however, in this instance, the actuating device or pushbutton 62 is arranged in an upper side wall of the container 12 diametrically opposite the face mask 20.

Figure 8:
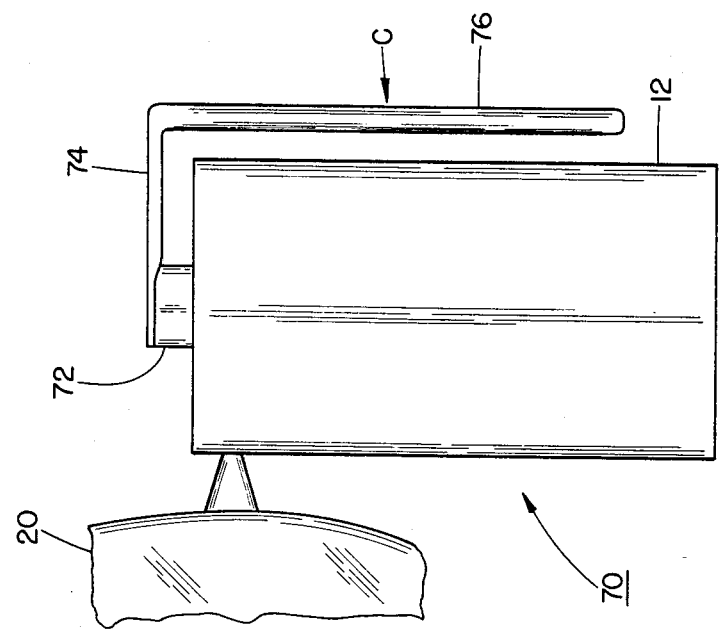

Finally, in the embodiment of FIG. 8 of the drawing, the breathing apparatus 70 has the face mask 20 connected to the container 12 in a manner similar to that shown in the embodiments of FIGS. 5 or 7; however, in this instance, the actuation of the valve 72 at the upper end of the container 12 for dispensing a flow of the gas into the face mask 20 is effected by means of an inverted L-shaped lever 74 having one arm portion fastened to the valve mechanism 72 and having a second depending lever arm portion 76 extending in coaxial spaced relationship along the cylindrical wall of the container 12, so that depression of the lever towards the container 12 in the direction of arrow C, by squeezing with one or more fingers of the hand holding the apparatus, will produce an actuation of the valve mechanism 72 and dispensing of a flow of gas from the container 12 into the face mask 20.

From the foregoing, it becomes readily apparent that the invention provides for an extremely simple and inexpensive portable breathing apparatus for supplying an emergency supply of an oxygen-rich gas, which to a considerable extent forms an additional protective measure for the occupants of a hotel, dwelling or office who may be trapped in a fire generating noxious and deadly fumes and smoke which could readily result in serious injuries or even death by asphyxiation. The breathing apparatus pursuant to the invention can be readily stored and prominently displayed in hotel rooms, offices and apartments at suitable locations, and its very simplicity in use renders it universally applicable even to persons who are not familiar with that type of device or are basically unskilled.

While there has been shown and described what are considered to be preferred embodiments of the invention, it will of course be understood that various modifications and changes in form or detail could readily be made without departing from the spirit of the invention. It is therefore intended that the invention be not limited to the exact form and detail herein shown and described, nor to anything less than the whole of the invention herein disclosed hereinafter claimed.

What is claimed is:

1. A portable breathing apparatus providing for an emergency supply of an oxygen-rich gas; comprising:
(a) a closed canister having a top closure portion and a circumferential side wall and containing a quantity of said oxygen-rich gas in a pressurized condition; a dispensing orifice for said gas on said canister; and externally-actuatable valve means in said canister for maintaining said dispensing orifice in a normally-closed condition;

(b) a face mask of a substantially transparent, plastic material adapted to receive the mouth, nose and eyes of a user; connector means on said face mask for fastening said face mask to said canister proximate the location of said discharge orifice; and flow passageway means extending through said connector means to communicate the interior of said face mask with the discharge orifice on said canister, whereby actuation by a user of said valve means will dispense a flow of said oxygen-rich gas from said canister into said face mask during the period of valve-actuation; and (c) said canister further containing a water admixed with said oxygen-rich gas, whereby actuation of said valve means causes a spray of water and gas to be ejected into said facemask through said dispensing orifice for moistening the mouth and nose of a user, and wherein a porous sponge is located in the lower interior portion of said facemask adapted to cover the mouth and nose of a user, said sponge encompassing the dispensing orifice on said canister, said sponge being permeable to said water and gas spray by inhibiting water from contacting the eyes of the user.

2. A breathing apparatus as claimed in claim 1, wherein said face mask is constituted of a resiliently-elastic material so as to have the rim portions thereof conform to the facial contours of a user upon external pressure being applied to said face mask during use thereof.

3. A breathing apparatus as claimed in claim 2, comprising sealing means extending about the face-contacting rim of said face mask to form a sealing edge when in contact with the face of a user.

4. A breathing apparatus as claimed in claim 1, wherein said canister includes a depressable pushbutton at the upper end thereof operatively connected to said valve means and namely maintaining said valve means in a shutoff condition, whereby depressing said pushbutton actuates said valve means to open the latter and facilitate flow of said gas through said dispensing orifice into said face mask.

5. A breathing apparatus as claimed in claim 4, wherein said pushbutton is arranged in said top closure portion of said canister.

6. A breathing apparatus as claimed in claim 4, wherein said pushbutton is arranged in the juncture between the top closure portion and the circumferential side wall of said canister.

7. A breathing apparatus as claimed in claim 1, wherein said canister includes an external, generally inverted L-shaped lever having one arm depending in coaxial spaced relationship along the circumferential wall of said canister and extending longitudinally thereof, said lever having the end of the other arm thereof operatively connected to said valve means whereby depression of said first lever arm towards the canister wall actuates said valve means for dispensing a flow of said gas from said canister into said face mask.

8. A breathing apparatus as claimed in claim 1, wherein said face mask is molded from a thermoplastic material.

9. A breathing apparatus as claimed in claim 1, wherein said gas in said canister is at a relatively low superatmospheric pressure.

10. A breathing apparatus as claimed in claim 1, wherein said canister is an aerosol-type cylindrical container.

* * * * *